United States Patent
Pasquet et al.

(10) Patent No.: US 7,087,083 B2
(45) Date of Patent: *Aug. 8, 2006

(54) SELF LOCKING FIXABLE INTERVERTEBRAL IMPLANT

(75) Inventors: Denis Pasquet, Pessac (FR); Régis Le Couedic, Bordeaux (FR); Jacques Senegas, Merignac (FR)

(73) Assignee: Abbott Spine, Bordeaux (FR)

(*) Notice: Subject to any disclaimer, the term of this patent is extended or adjusted under 35 U.S.C. 154(b) by 226 days.

This patent is subject to a terminal disclaimer.

(21) Appl. No.: 10/471,213

(22) PCT Filed: Mar. 13, 2002

(86) PCT No.: PCT/FR02/00888

§ 371 (c)(1),
(2), (4) Date: Sep. 8, 2003

(87) PCT Pub. No.: WO02/071960

PCT Pub. Date: Sep. 19, 2002

(65) Prior Publication Data

US 2004/0117017 A1    Jun. 17, 2004

(30) Foreign Application Priority Data

Mar. 13, 2001  (FR) .................... 01 03362

(51) Int. Cl.
*A61F 2/44* (2006.01)

(52) U.S. Cl. ................. 623/17.11; 606/61

(58) Field of Classification Search .. 623/17.11–17.16; 606/61, 74
See application file for complete search history.

(56) References Cited

U.S. PATENT DOCUMENTS

| 5,356,412 A | * | 10/1994 | Golds et al. .................. 606/74 |
| 5,496,318 A | | 3/1996 | Howland et al. |
| 6,302,889 B1 | * | 10/2001 | Keller .......................... 606/74 |
| 6,514,256 B1 | * | 2/2003 | Zucherman et al. .......... 606/61 |
| 6,656,185 B1 | * | 12/2003 | Gleason et al. ............... 606/74 |
| 2004/0024458 A1 | * | 2/2004 | Senegas et al. .......... 623/17.11 |

FOREIGN PATENT DOCUMENTS

| FR | 2 704 745 A | | 11/1994 |
| FR | 2717675 | * | 9/1995 |
| FR | 2 722 088 | | 1/1996 |
| FR | 2 775 183 | | 8/1999 |

* cited by examiner

*Primary Examiner*—Pedro Philogene
*Assistant Examiner*—Michael J. Araj
(74) *Attorney, Agent, or Firm*—Dennis G. LaPointe

(57) ABSTRACT

An intervertebral implant which includes a block (10) with two grooves (12, 14) on opposite sides and on the longitudinal axis (A) of the block (10). The block (10) has two lateral walls and a fixing tie (16), where a first end (20) of the fixing tie (16) is adapted to be connected to the block (10) and a second end (28) of the fixing tie is a free end. The intervertebral implant includes a removable self-locking fixing member (30, 32) which is connectable with studs (34) and through which the fixing tie (16) can slide. A lateral wall (36) of the block (10) includes housings (38) adapted to cooperate with the (34) to connect the removable self-locking fixing member (30, 32) to the lateral wall (36) of the the block (10).

19 Claims, 2 Drawing Sheets

SELF LOCKING FIXABLE INTERVERTEBRAL IMPLANT

FIELD OF THE INVENTION

The present invention relates to an intervertebral implant comprising a block with grooves on two opposite sides and on a longitudinal axis of said block to receive the spinous processes of two vertebrae. The block has two lateral walls and at least one fixing tie for retaining said spinous processes in said grooves.

BACKGROUND OF THE INVENTION

Intervertebral implants comprising a block which is inserted between the spinous processes which extend the posterior portion of two vertebrae, to limit their movement towards each other, are well known to the person skilled in the art. Installing such implants on the spine necessitates a lengthy surgical procedure during which the intervertebral ligament connecting the two vertebrae between which the block is to be inserted is extracted and openings for inserting the ties are formed under the intervertebral ligaments, in the upper and lower intervertebral space. Before the tie is inserted between the spinous processes a first end of the tie is connected to said block, for example to at least one of the flanges of said groove, after which the tie is fed into the intervertebral opening and around the spinous process; it is then connected to the other flange of the groove. Thus the tie retains the spinous process in the groove of the block.

A single tie can be used to secure the block, in which case it extends over the lateral wall of the block as far as one of the flanges of the opposite groove and then around the other spinous process, so that it can be connected to the other flange of the opposite groove.

Although installing the block between the two spinous processes is relatively quick and easy, attaching the ties to the block is much more difficult, because of the lack of room in the intervertebral space, and so forming loops and tying knots is relatively time-consuming and represents a non-negligible part of the duration of the procedure.

An object of the present invention is to provide an intervertebral implant including a block and a tie and which can be installed quickly and easily.

SUMMARY OF THE INVENTION

To this end, the present invention provides an implant comprising a removable self-locking fixing member having first connecting means and through which said tie can slide when it is moved in translation in a first direction, said self-locking fixing member being adapted to immobilize said tie against movement in translation in a second direction opposite said first direction, and wherein at least one of two lateral walls of said block includes second connecting means adapted to cooperate with said first connecting means to connect said removable self-locking fixing member to the lateral wall of said block, movement of said free end of said tie to move said tie in translation in said first direction causing said spinous process to be clamped in said groove and said tie to be immobilized against movement in translation relative to said block in said second direction.

Accordingly, a characteristic of an implant according to the invention is the method of attaching said tie to said block, after the block has been inserted between the two spinous processes, by means of the removable self-locking fixing member of the first connecting means, which is adapted to be connected to said block, which is provided with second connecting means. Thus said tie, whose first end is connected to the block, is inserted into the intervertebral space above or below the intervertebral space in which the block is fitted, after which the free second end of said tie is inserted into said removable self-locking fixing member, outside the body of the patient. The removable self-locking fixing member is then offered up to the lateral wall of the block, the surgeon at the same time sliding the tie through said member, which is then connected to the block through co-operation of the first and second connecting means. The tie passing around the spinous process to retain it in the groove of the block is tightened after the removable self-locking fixing member has been connected to the block. When the free second end of the tie moves in translation in the first direction, the tension in the tie inside the removable self-locking fixing member induces a pressure which immobilizes said tie against movement in translation in a second direction opposite the first direction.

In one particular embodiment of the invention said removable self-locking fixing member has a first main face opposite a second main face, which main faces are joined together at two ends of said removable self-locking fixing member, and a central slot opening into said main faces and through which said tie passes, so that a first portion of said tie between said first end and said central slot can press a second portion of said tie between said central opening and said free second end of said tie against a portion of said first main face adjoining the first end of said self-locking fixing member to retain said tie in a fixed position relative to said self-locking fixing member.

Accordingly, the tie partly surrounds the removable fixing member so that a first portion faces the first main face, the tie bears on the second end of said fixing member and passes through the central slot, and a second portion exiting onto said first main face is disposed between said first main face and said first tie portion, parallel to the latter. As a result, said first tie portion, which leads on directly from a tie portion around the spinous process and is guided substantially in a plane containing said first main face aligned with the first end of said fixing member, is tensioned by pulling the free second end of said tie, which leads on from the second tie portion between the first tie portion and the first main face. The tighter the tie is pulled, the stronger said first tie portion presses the second tie portion against the first main face and holds it in a fixed position relative to said removable self-locking fixing member.

According to a particularly advantageous characteristic of the invention, said removable self-locking fixing member has a central slot whose median plane is at an acute angle to said first portion of said first main face to form an edge in each of the main faces adapted to form first friction means for said tie. Accordingly, movement of said tie in translation in said self-locking fixing member is resisted both by the corner formed by the inside wall of the central slot and said first portion of said first main face, and by the corner formed by the inside wall of the central slot and a portion of the second main face. Also, the second end of said removable self-locking fixing member against which said tie bears advantageously has two faces inclined to each other to form an edge adapted to form second friction means for said tie.

In a preferred embodiment of the invention, said second connecting means comprise a housing in said lateral wall of said block whose two opposite edges, which are substantially parallel to said axis of the block, include abutment means substantially perpendicular to said lateral wall of said block, and said first connecting means project from lateral sides of said removable self-locking fixing member to bear against said abutment means to immobilize said removable self-locking fixing member against movement in translation relative to said block in a direction substantially parallel to said longitudinal axis and corresponding to said second direction of immobilization of said tie against movement in translation relative to said block.

Accordingly, the removable self-locking fixing member can be at least partly mortised into a housing and immobilized against movement in translation in a direction substantially parallel to the longitudinal axis of said block, in particular in said second direction, corresponding to tightening said tie onto the spinous process. Because the first connecting means project from the lateral sides of said fixing member, they bear against the abutment means when said tie is pulled to tighten it.

Said housing preferably has an open end facing said first end of the removable self-locking fixing member and through which said tie can slide. Accordingly, said tie can be guided by the walls of said open end when it is moved in translation, to press said second tie portion against it, so that said tie remains substantially in a plane containing said first main face. The tie portion facing the first main face is extended, on the one hand, towards the spinous process and, on the other hand, towards said second end, to surround it and press it against said first main face portion after passing through said slot, said tie forming a loop whose two ends exit onto said open end.

In a preferred embodiment of the invention, said abutment means consist of at least two facing oblong openings substantially perpendicular to said lateral wall of the block in two opposite edges of said housing, and said first connecting means consist of studs projecting from the lateral sides of said self-locking fixing member and aligned with each other, so that they can be inserted into said oblong openings perpendicularly to said lateral wall.

In this way, when said tie is moved in translation to clamp the spinous process in said groove, the self-locking fixing member is entrained in translation in a direction parallel to said second direction and said studs bear against the edge of the oblong openings to immobilize said member. Said oblong openings advantageously have an elastically deformable constricted portion between an entry portion and a closed end portion and adapted to be deformed by forcibly pressing in said stud so that said stud is held fixed in position in said closed end portion. As a result of this, said removable self-locking fixing member is fastened particularly strongly to said lateral wall simply by pressing on it, which facilitates fitting.

Said implant advantageously includes two ties respectively adapted to surround an upper spinous process and a lower spinous process and two removable self-locking fixing members adapted to be connected to two lateral walls of said block. Accordingly, the processes are connected to said block independently of each other.

In a particularly advantageous embodiment of the invention, said block and said removable self-locking fixing member are made of plastics materials.

Other features and advantages of the invention will emerge from a reading of the following description of particular embodiments of the invention, which is given by way of non-limiting illustrative example and with reference to the drawings, in which:

DETAILED DESCRIPTION OF THE INVENTION

Figure 1:
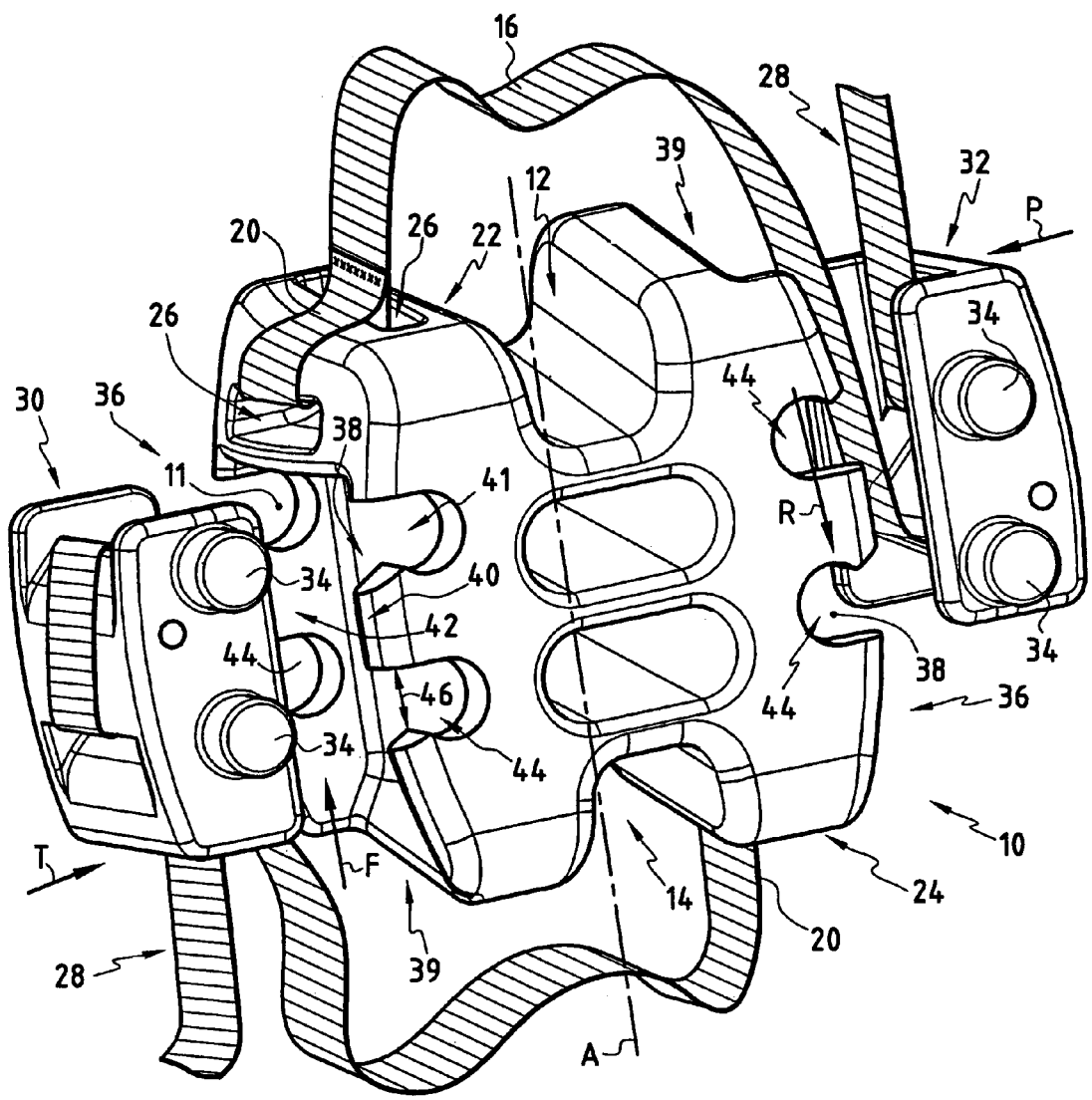
FIG. 1 is a diagrammatic exploded side view of an implant according to the invention.

FIG. 1 shows an intervertebral implant including a block 10 having a longitudinal axis A on which there are a top groove 12 and a bottom groove 14, the two grooves 12 and 14 being on opposite sides of the block. Each of the grooves 12 and 14 is adapted to receive a spinous process and the block is mounted between the spinous processes of two vertebrae to limit their movement towards each other.

The implant further includes two ties 16 and 18 in the form of tapes, and the first ends of these ties are connected to respective diagonally opposite flanges 22 and 24. The connection between the first end 20 of a tie and the respective flange 22, 24 is obtained by means of a bore 26 passing through the end of the flange 22, 24 and by sewing the first end to form a loop through the bore. As a general rule, the first ends 20 of the ties 16 and 18 are mounted symmetrically on the flanges 22 and 24 before starting the surgical procedure.

One feature of the implant is the method of attaching the second ends of the ties 28 by means of two removable self-locking fixing members 30, 32 through which the respective ties 18 and 16 can slide in directions F and R. On the other hand, and as explained in more detail hereinafter, when they are taut the ties 18 and 16 are immobilized against movement in translation in the directions opposite the directions F and R.

Apart from the fact that they are used to attach the ties 16, 18 to the block 10, the removable self-locking fixing members 30, 32 can be connected to the block 10 after the latter has been installed in the intervertebral space and the ties 16 and 18 have been inserted into the removable self-locking fixing members 30, 32.

To this end, the removable self-locking fixing members 30, 32 have first connecting means 34 taking the form of studs projecting from the lateral sides of the fixing members 30, 32. FIG. 1 shows one face of the intervertebral implant whose other face, which is symmetrical to the former face with respect to a vertical plane, cannot be seen in FIG. 1. Thus the studs 34 have symmetrically disposed counterparts on the lateral sides of the fixing members 30, 32. Also, the lateral walls 36 of the block 10 includes second connecting means forming a housing 38 of which at least one end 39 is open and whose two opposite edges 40 and 42 are parallel to each other and to the axis A of the block 10 and have oblong openings 44 forming abutments. Of course, the width of the housing 38 between the two opposite edges 40, 42 is greater than the width of the fixing members 30, 32 between the two opposite lateral sides, so that the fixing members 30, 32 are at least partly mortised into said housings 38.

The opposite edges 40 and 42 of the housing 38 have two pairs of facing oblong openings adapted to cooperate with the studs 34 projecting from the lateral sides of the fixing members 30, 32. Accordingly, the distance between the two oblong openings on one edge 40 or 42 is substantially equivalent to the distance between two studs 34 on a lateral side of a fixing member 30 or 32.

Also, the oblong openings 44 have a deformable constriction 46 between their entry and their closed end so that the studs 34, whose diameter is significantly greater than the width of the constriction 46, can be forced into the oblong openings 44. Obviously, the width of the closed end of the oblong openings corresponds to the diameter of the studs 34.

The block 10 and the fixing members 30, 32 are made of plastics materials and have a sufficiently low modulus of elasticity for the constriction 46 and the stud 34 to deform elastically and at the same time so that the stud is inserted into the closed end of the oblong opening 44. The foregoing explanation of the cooperation of a stud 34 with an oblong opening 44 obviously applies to all the studs 34 and all the oblong openings 44. Thus the removable self-locking fixing members 30 and 32 can be mortised into their respective housings 38, in the direction T for the member 30 and in the direction P for the member 32. When the members 30, 32 are mortised into the lateral walls of said block 10, the four studs 34 are located at the closed ends of the four oblong openings 44 and can be withdrawn only by applying traction to the member 30 or 32 and to the block 10 to deform the constriction 46 again.

Figure 2:
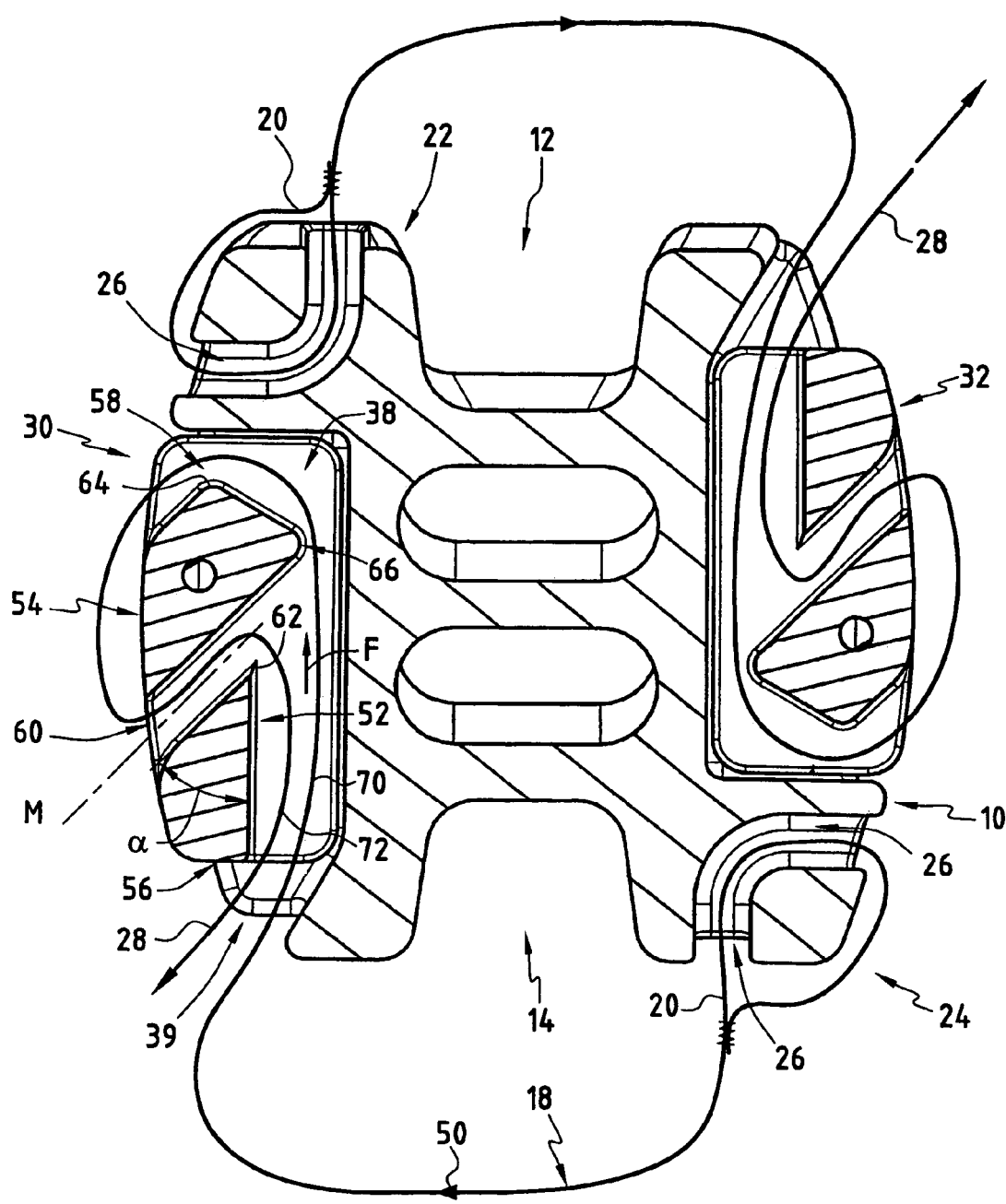
FIG. 2 is a diagrammatic view in vertical section of the implant in accordance with the invention shown in FIG. 1, after installation.

FIG. 2 shows the intervertebral implant when the two fixing members 30 and 32 are mortised into their respective housings 38. The component parts of the self-locking fixing members for immobilizing the ties 16 and 18 against movement in translation are described next with reference to FIGS. 1 and 2.

The following description refers to the removable self-locking fixing member 30, but applies identically to the fixing member 32.

FIG. 2 shows again the tie 18 whose first end 20 is connected to the flange 24 and a portion 50 of which faces the groove 14 in which a spinous process, not shown, can be supported. The tie 18 then extends towards the other flange of the groove 14, where it rejoins the self-locking fixing member 30. As explained above, the tie 18 is inserted into the fixing member 30 before it is mortised-into the housing 38.

The self-locking fixing member 30 has a first main face 52 opposite a second main face 54, the two opposite faces 52, 54 meeting at a first end 56 and at a second end 58 of the fixing member 30, which also has a central slot 60 opening into the first main face 52 and into the second main face 54. The median plane M of the slot 60 is at an acute angle α to the first portion of the main face, for example an angle of 30°, to form an edge 62. Furthermore, the second end 58 of the fixing member 30 has two faces inclined relative to each other, forming an edge 64. Also, the opening of the slot 60 is at the junction between the first main face and the second end 58, thereby forming another edge 66.

The components previously described immobilize the tie 18 against movement in translation relative to said fixing member 30 and consequently relative to the block 10, since the fixing member 30 is immobilized in the housing 38.

To this end, and before inserting the removable self-locking fixing members into the lateral walls of the block 10, the free end 28 of the tie 18 is inserted, for example after it has been passed behind the intervertebral ligament in the lower intervertebral space, into the central slot 60, from the second main face 54 of the fixing member 30 and outside the body of the patient. The fixing member 30 is then offered up to the lateral wall of the block 10, by sliding it along the tie 18 and placing it so that the first main face is opposite the lateral wall and the portion of the tie 18 coming from the lower intervertebral space and the portion of the tie 18 extended by the free second end 28 exit into the open end 39, of the fixing member 30. Accordingly, a portion of the tie 18 coming from the lower intervertebral space is pressed against the first main face of the fixing member 30 and then circumvents the second end 58 and is pressed against a portion of the second main face 54, before it passes through the central slot, after which it exits onto the first main face 52 and is pressed against a portion of the first main face 52 which adjoins the first end 56.

In this way, if the free second end 28 of the tie 18 is pulled in order to tension it and to fasten together the spinous process and the block 10, a first portion 70 of the tie 18 presses a second portion 72 of the tie 18 against the first main face and produces friction forces that immobilize the portions 70 and 72 of the tie 18 relative to each other. The tie 18 is shown as a line in FIG. 2, to simplify the drawing, but the tie 18 has a thickness such that contact between the two portions 70 and 72 is possible with this configuration of the fixing member 30 and the block 10.

The more the tie 18 is tensioned in the fixing member 30, the more the two portions 70 and 72 of the tie 18 are pressed together and the more effective at immobilizing the tie against movement in translation in a direction opposite to the direction F are the friction means formed by the edges 62 or 66, for example. In this way the tie 18 is immobilized against movement in translation relative to the block 10 and secures the block 10 to the spinous process.

Of course, in a totally symmetrical fashion, the block 10 is held against the other spinous process by means of the tie 16 and the fixing member 32.

The invention claimed is:

1. An intervertebral implant to be placed between spinous processes of two vertebrae comprising:
    a block having two opposite sides in the direction of a longitudinal axis, each side being provided with a groove adapted to receive said spinous processes, said block further having two lateral walls;
    a fixing tie for retaining said spinous processes in said grooves, said fixing tie having a first end adapted to be connected to said block and a second free end, said fixing tie being adapted to surround at least one spinous process;
    a removable self-locking fixing member having first connecting means and through which said fixing tie can slide when it moves in translation in a first direction, said self-locking fixing member being adapted to immobilize said fixing tie against movement in translation in a second direction opposite said first direction; and
    at least one of said lateral walls of said block including second connecting means to cooperate with said first connecting means to connect said removable self-locking fixing member to said at least one of said lateral walls, a movement of said free end of said fixing tie to move said fixing tie in translation in said first direction causing said spinous process to be clamped in said groove and said fixing tie to be immobilized against movement in translation relative to said block in said second direction.

2. The intervertebral implant according to claim 1, wherein said removable self-locking fixing member has a first main face opposite a second main face, said main faces being joined together at two ends of said removable self-locking fixing member and a central slot opening into said main faces and through which said fixing tie passes, so that a first portion of said tie between said first end and said central slot can press a second portion of said fixing tie between said central opening and said free second end of said fixing tie against a portion of said first main face adjoining the first end of said self-locking fixing means to retain said fixing tie in a fixed position relative to said self-locking fixing member.

3. The intervertebral implant according to claim 2, wherein the central slot of said removable self-locking fixing member has a median plane which is at an acute angle (a) to said first portion of said first main face to form an edge in each of the main faces adapted to form first friction means for said fixing tie.

4. The intervertebral implant according to claim 2, wherein said second end of said removable self-locking fixing member against which said fixing tie bears has two faces inclined to each other to form an edge adapted to form second friction means for said fixing tie.

5. The intervertebral implant according to claim 1, wherein said second connecting means include a housing in said at least one of said lateral walls of said block having two opposite edges, which are substantially parallel to said longitudinal axis of the block, said edges including abutment means substantially perpendicular to said at least one of said lateral walls of said block, and said first connecting means project from lateral sides of said removable self-locking fixing member to bear against said abutment means to immobilize said removable self-locking fixing member against movement in translation relative to said block in a direction substantially parallel to said longitudinal axis and corresponding to said second direction of immobilization of said fixing tie against movement in translation relative to said block.

6. The intervertebral implant according to claim 5, wherein said housing has an open end facing said first end of the removable self-locking fixing member and through which said fixing tie can slide.

7. The intervertebral implant according to claim 5, wherein said abutment means consist of at least two facing oblong openings substantially perpendicular to said at least one of said lateral walls of the block in two opposite edges of said housing, and said first connecting means consist of studs projecting from the lateral sides of said self-locking fixing member and aligned with each other, so that said studs can be inserted into said oblong openings perpendicularly to said at least one of said lateral walls.

8. The intervertebral implant according to claim 7, wherein said oblong openings have an elastically deformable constricted portion between an entry portion and a closed end portion and adapted to be deformed by forcibly pressing in said stud so that said stud is held fixed in position in said closed end portion.

9. The intervertebral implant according to claim 1, further comprising a second fixing tie and a second removable self-locking fixing member, wherein both fixing ties are respectively adapted to surround an upper spinous process and a lower spinous process and both removable self-locking fixing members adapted to be connected to two lateral walls of said block.

10. The intervertebral implant according to claim 1, wherein said block and said removable self-locking fixing member are made of plastics materials.

11. An intervertebral implant to be placed between spinous processes of two vertebrae comprising:

a block having two opposite sides in the direction of a longitudinal axis, each side being provided with a groove adapted to receive said spinous processes, said block further having two lateral walls;

a fixing tie for retaining said spinous processes in said grooves, said fixing tie having a first end adapted to be connected to said block and a second free end, said fixing tie being adapted to surround at least one spinous process;

a removable self-locking fixing member having first connecting means and through which said fixing tie can slide when it moves in translation in a first direction, said self-locking fixing member being adapted to immobilize said fixing tie against movement in translation in a second direction opposite said first direction; and at least one of said lateral walls of said block including second connecting means to cooperate with said first connecting means to connect said removable self-locking fixing member to said at least one of said lateral walls, a movement of said free end of said fixing tie to move said fixing tie in translation in said first direction causing said spinous process to be clamped in said groove and said fixing tie to be immobilized against movement in translation relative to said block in said second direction, wherein said second connecting means include a housing in said at least one of said lateral walls of said block having two opposite edges, which are substantially parallel to said longitudinal axis of the block, said edges including abutment means substantially perpendicular to said at least one of said lateral walls of said block, and said first connecting means project from lateral sides of said removable self-locking fixing member to bear against said abutment means to immobilize said removable self-locking fixing member against movement in translation relative to said block in a direction substantially parallel to said longitudinal axis and corresponding to said second direction of immobilization of said fixing tie against movement in translation relative to said block.

12. The intervertebral implant according to claim 11, wherein said housing has an open end facing said first end of the removable self-locking fixing member and through which said fixing tie can slide.

13. The intervertebral implant according to claim 11, wherein said abutment means consist of at least two facing oblong openings substantially perpendicular to said at least one of said lateral walls of the block in two opposite edges of said housing, and said first connecting means consist of studs projecting from the lateral sides of said self-locking fixing member and aligned with each other, so that said studs can be inserted into said oblong openings perpendicularly to said at least one of said lateral walls.

14. The intervertebral implant according to claim 13, wherein said oblong openings have an elastically deformable constricted portion between an entry portion and a closed end portion and adapted to be deformed by forcibly pressing in said stud so that said stud is held fixed in position in said closed end portion.

15. The intervertebral implant according to claim 11, wherein said removable self-locking fixing member has a first main face opposite a second main face, said main faces being joined together at two ends of said removable self-locking fixing member and a central slot opening into said main faces and through which said fixing tie passes, so that a first portion of said tie between said first end and said central slot can press a second portion of said fixing tie between said central opening and said free second end of said fixing tie against a portion of said first main face adjoining the first end of said self-locking fixing means to retain said fixing tie in a fixed position relative to said self-locking fixing member.

16. The intervertebral implant according to claim 15, wherein the central slot of said removable self-locking fixing member has a median plane which is at an acute angle ($\alpha$) to said first portion of said first main face to form an edge in each of the main faces adapted to form first friction means for said fixing tie.

17. The intervertebral implant according to claim 15, wherein said second end of said removable self-locking fixing member against which said fixing tie bears has two faces inclined to each other to form an edge adapted to form second friction means for said fixing tie.

18. The intervertebral implant according to claim 11, further comprising a second fixing tie and a second removable self-locking fixing member, wherein both fixing ties are respectively adapted to surround an upper spinous process and a lower spinous process and both removable self-locking fixing members adapted to be connected to two lateral walls of said block.

19. The intervertebral implant according to claim 11, wherein said block and said removable self-locking fixing member are made of plastics materials.

* * * * *